United States Patent [19]

Kahn et al.

[11] Patent Number: 5,318,895
[45] Date of Patent: Jun. 7, 1994

[54] ASPERGILLUS NIGER MUTANTS

[75] Inventors: Jennifer N. Kahn, East Brunswick; Kevin M. Byrne, West Trenton, both of N.J.; Louis Kaplan, New City, N.Y.; Richard J. Monaghan, Somerset, N.J.

[73] Assignee: Merck & Co., Inc., Rahway, N.J.

[21] Appl. No.: 956,716

[22] Filed: Oct. 5, 1992

[51] Int. Cl.$^5$ .................... C12Q 1/18; C12N 1/00; C07D 498/00

[52] U.S. Cl. .................... 435/32; 435/29; 435/119; 435/911; 435/913; 435/917; 514/291; 540/456

[58] Field of Search ............ 435/32, 29, 911, 193, 435/917, 119; 514/291; 540/456

[56] References Cited

U.S. PATENT DOCUMENTS

| | | | |
|---|---|---|---|
| 3,929,992 | 12/1975 | Sihgal et al. | 514/291 |
| 4,894,366 | 1/1990 | Okuhara et al. | 514/291 |
| 5,093,338 | 3/1992 | Byrne et al. | 514/291 |
| 5,138,052 | 8/1992 | Chen et al. | 540/456 |
| 5,210,030 | 5/1993 | Petuch et al. | 435/119 |

FOREIGN PATENT DOCUMENTS

WO92/14737  3/1992  PCT Int'l Appl. ........ C07D 498/18

OTHER PUBLICATIONS

Braude, *Infectious Diseases and Medical Microbiology*, 2nd edition, Published by W. B. Saunders Company 1986, Chapter 79, pp. 592–597.

Kirkland et al, *Antimicrobiol Agents and Chemotherapy*, vol. 24, No. 6, pp. 921–924, 1983.

Matsen et al. *Manual of Clinical Microbiology*, 2nd edition, Published by American Society for Microbiology, 1974, Chapter 46, pp. 418–427.

Gause et al, *Chemical Abstracts*, vol. 113, Reference No. 94510t, 1990.

*Primary Examiner*—Michael G. Wityshyn
*Assistant Examiner*—Abdel A. Mohamed
*Attorney, Agent, or Firm*—Charles M. Caruso; J. Eric Thies

[57] ABSTRACT

Disclosed are new *Aspergillus niger* mutants which can be used for identifying active FK-506/ rapamycin type, or cyclosporin A type immunosuppressants in a broth, natural product extract, or composition exhibiting immunosuppressant activity. Specifically disclosed are the new mutants, ATCC No. 74085 (MF 5659), which is sensitive to FK-506 and rapamycin but resistant to cyclosporin A; ATCC No. 74086 (MF 5659) which is resistant to FK-506, cyclosporin A and rapamycin; and ATCC No. 74087 (MF 5661) which is resistant to FK-506 and rapamycin, but sensitive to cyclosporin A.

6 Claims, No Drawings

ASPERGILLUS NIGER MUTANTS

BACKGROUND OF THE INVENTION

1. Field of the Invention

This invention relates to new *Aspergillus niger* mutants for identifying active FK-506/rapamycin type or cyclosporin A type immunosuppressants. Specifically disclosed are the new mutants, *Aspergillus niger*, (Merck Culture Collection No. MF 5659) ATCC No. 74085; ATCC No. 74086 (MF 5660); and ATCC No. 74087 (MF 5661).

2. Brief Description of Disclosures in the Art

In 1983, the US FDA approved cyclosporin A, (see U.S. Pat. No. 4,117,118 to Sandoz) an effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, now issued as U.S. Pat. No. 4,894,366 hereby incorporated by reference, describes a new macrolide immunosuppressant FK-506 which is reputed to be 100 times more effective than cyclosporin. The macrolide is produced by fermentation of a particular strain of *Streptomyces tsukubaensis*. Also described is the closely related macrolide immunosuppressant FK-520, (FK-900520) produced by *S. hygroscopicus* subsp. *yakushimaensis*.

U.S. Pat. No. 3,929,992 to Ayerst discloses the macrolide compound rapamycin and its antibiotic and antifungal properties. Recent publications, (see J. of Immunology Vol. 144, p. 251-258 (No. 1), Jan. 1990 by F. J. Dumont et. al.,) disclose the use of the compound additionally as an immunosuppressant.

In the search for new immunosuppressant analogs, it would be helpful to have a single, convenient diagnostic assay, not involving laboratory animals, to selectively establish the presence of either FK-506/rapamycin type or cyclosporin A type immunosuppressant activity, in an unknown fermentation broth, natural product extract, e.g. human serum, plant extracts, or unknown composition, which displays immunosuppressant activity.

SUMMARY OF THE INVENTION

By this invention there is provided biologically pure cultures of new *Aspergillus niger* mutants, specifically, *Aspergillus, niger* (MF 5659) ATCC. No. 74085; ATCC No. 74086) (deposited Aug. 14, 1991) deposited Aug. 14, 1991) (MF5660); and ATCC No. 74087 (deposited Aug. 14, 1991) (MF 5661).

Further provided is a processes, i.e. diagnostic assay, to distinguish between FK-506/ rapamycin-type activity and cyclosporin A Type immunosuppressant activity utilizing the above microorganisms.

DETAILED DESCRIPTION OF THE INVENTION AND PREFERRED EMBODIMENTS

The present invention involves the above-described *Aspergillus niger* mutants and their parent, ATCC No. 6275, useful for diagnostically assaying for the presence of either FK-506/rapamycin or cyclosporin A type immunosuppressant activity in an unknown broth, natural product extract, or unknown biological composition.

The mutants can be used in combination with their parent, e.g., combination of ATCC No. 74088 and ATCC No. 6275 to detect for cyclosporin A; ATCC No. 74087 and ATCC No. 6278 to detect for the presence of FK-506/rapamycin type activity.

Also, they can be used in combination with each other, e.g., ATCC Nos. 74085, 74086, 74087 and 6275 to detect for the individual or simultaneous presence of FK-506/rapamycin or cyclosporin A types activity in an unknown broth or composition.

The mutants can be further used to identify improved FK-506 producing microorganism strains. For example, the above combination of ATCC No. 74087/ATCC No. 6275 can be used to distinguish between low and high FK-506 producing microorganisms by comparing the respective zones of inhibition (ZOI), as described below.

To further distinguish specifically between FK-506 and rapamycin type activity, recourse can be had to the methods utilizing *Saccharomyces cerevisiae* mutants as described in Molecular and Cellular Biology, Vol. 11, No. 9, Sept. 1991, p. 4616-4626 by L. Brizuela et al.

The *Aspergillus niger* microorganisms are currently on deposit with the American Type Culture Collection, 12301 Parklawn Drive in Rockville, Maryland as indicated by the herein described ATCC Nos., and in the Merck Culture Collection at Rahway, New Jersey as indicated by the respective MF Nos.

The taxonomic and biological characteristics for each microorganism are very similar and are briefly and generally described herein below. The most useful method of distinguishing between the microorganisms is on the basis of their respective sensitivities toward the immunosuppressant drugs: FK-506, rapamcycin and cyclosporin A, as described herein.

Colonies growing slowly; attaining a diameter of 30-32 nun on Czapek's agar; 34-36 mm on malt-extract agar in 5 days at 27° C. On Czapek's agar, mycelium is loose, hyaline, submerged, bearing abundant erect conidiophores, black to dark brown black, Blackish Brown, Chaetura Black, Plumbeous Black, (capitalized colors names are from Ridgway, R. 1912. Color Standards and Nomenclature. Published by the author, Washington, D.C., 1912) reverse colorless. Conidial heads at first globose, conidial columns soon splitting to appear radiate, biseriate with conidiogeneous cells borne on metulae. Conidiophores arising from a foot cell, either from submerged hyphae in the agar or from aerial mycelium, 1000-1500 $\mu m \times 13-15$ $\mu n$, smooth, colorless or pale brown, terminating in vesicles. Vesicles globose to subglobose, 47-55 $\mu n$ in diameter. Conidiogenous cells, enteroblastic, phialidic, cylindrical with truncate or slightly tapered apices, 5.7-7.6- $\times 3-3.4$ $\mu n$. Metulae short cylindrical, 11.4-19$\times$4.5-5.5 $\mu n$. Conida subglobose to globose, brown, 3.4-3.8 $\mu n$ in diameter, echinulate. Sclerotia, cleistothecia and Hulls cells absent.

These strains can be assigned to Raper and Fennell's *Aspergillus niger* group (K. B. Raper and D. I. Fennell, 1965. The Genus *Aspergillus*, Williams & Wilkins Co., Baltimore) based on the black colony colors, biseriate and radiate conidial heads; globose vesicles; and globose, echinulate conidia. *A. niger* is separated from the other species in this group on conidial characteristics.

The mutant microorganisms and their parent can be used in immunosuppressant diagnostic assays.

To illustrate their utility potential their microbiological sensitivities are listed in the following Table:

TABLE

| ATCC No. | Acronym | Sinsitivity | |
|---|---|---|---|
| | | FK-506/Rap. | CsA |
| 74085 | CsA-R | + | − |
| 74086 | All-R | − | − |
| 74087 | FK-506/Rap-R | − | + |
| 6275 | All-S | + | + |

+ indicates sensitivity
− indicates resistance
CsA-R represents Cyclosporin A resistance
All-R represents resistance to all three drugs
FK-506/Rap represents FK-506/Rapamycin resistant
All-S represents sensitivity to all three drugs It is seen from the above Table, that combinations of sensitive/resistant strains to either CsA or FK-506/Rapamycin can be used as a basis for their individual diagnostic assays.

In general, if the *A. niger* microorganism contains a major binding protein for the particular immunosuppressant drug, eg. FK- 506, rapamycin, CsA, then the microorganism will be sensitive to the drug; otherwise, lack of the binding protein confers resistance.

The FK-506/Rapamycin resistant strain, ATCC No. 74087, in conjunction with the sensitive parent, *A. niger* 6275 or with the CsA-Resistant strain, ATCC No. 74085, can be used in the disc diffusion assay described in Example 2 to detect and validate the presence in broths, natural product extracts, or any other unknown biological medium of the FK-506 or rapamycin class of compounds <i.e., those binding to the major FK binding protein, FKBP12, see Siekierka, J. et. al. Nature, vol. 341, pp. 755–757 (1989).

Conducting the general disc diffusion assay, described in Example 2, using the combination: ATCC No. 74087/ATCC No. 6275 in the presence of a FK-506 or rapamycin type immunosuppressant will exhibit no zone of inhibition (ZOI) with ATCC No. 74087, but a measurable ZOI with ATCC No. 6275.

The area where conidiation (hyphal branching or coiling leading to the production of spores) is occurring will appear black. Where conidiation is inhibited, the zone surrounding the disc, usually circular will appear yellow. Thus, an advantage using *A. niger* mutants as opposed to, e.g. yeast, is that the ZOI will appear yellow as opposed to clear, and be more readily observable, especially in large assays.

The CsA-Resistant strain, ATCC No. 74085 in conjunction with the *A. niger* 6275 or with the FK-506/Rap strain, ATCC No. 74087, can be used to detect and validate the presence of the cyclosporin class of compounds (those binding to the major CsA binding protein, cyclophilin) (See Handschumacher, R. E. et al., Science 226, p. 544–546 (1984)).

Conducting the general disc diffusion assay described in Example 2 using the combination: ATCC Nos. 74085 and 6275 in the presence of a Cyclosporin A type immunosuppressant will exhibit no ZOI with 74085 but a measurable ZOI with 6275.

The disc diffusion assay can be used with the doubly resistant strain ATCC 74086 as a counterscreen of a new active found against *A. niger* 6275 to eliminate compounds of both FK-506/Rapamycin and cyclosporin A classes simultaneously. In this instance, the new active is most likely a member of a new structural class of immunosuppressants.

The above assay using ATCC Nos. 74087/6275 can also be used to distinguish between low and high FK-506 producing microorganisms. Particularly it can be used where an FK-506 producing parent microorganism is mutated to produce a mutant which displays a larger ZOI than the parent in broths produced from equivalent concentrations. The fact that there is no accompanying ZOI with the 74087 resistant microorganism for both the parent and mutant, would indicate that probably the increase in ZOI in the case of the mutated parent is due mainly to an increase in FK-506 immunosuppresant activity rather than some other casue or immunosuppressant structural class. However, a ZOI appearing also with the 75087 mutant would indicate the possibility of some other class of immunosuppressant activity.

The diagnostic assay described herein should be carried under totally aseptic, sterile conditions. A standard disc diffusion plate which is essentially a circular piece of filter paper is used to contact the unknown broth, natural product extract, and the like, usually being aqueous, to saturate the paper disc. Alternatively, a composition or compound is dissolved in an organic solvent or aqueous/organic solvent saturating the disc paper, then gently heated, or air-dried to remove the solvent.

The filter paper is then placed on top of an agar nutrient medium containing the specific A. niger microorganism(s) uniformly spread on top of the agar medium, e.g., YME. After incubating the system at 25°–30° C. for 1–3 days, the area surrounding the disc is observed. The surrounding *A. niger* microorganism will form a continuous black "lawn" in the region of the disc, if no drug is present to which it is sensitive. If the microorganism is sensitive, a yellow circular zone of inhibition (ZOI) will appear indicating activity of the FK-506/Rapamycin class or Cyclosporin A class. Alternatively, more than one disc can be employed for the same microorganism. For example, three discs, one for FK-506, rapamycin, cyclosporin A, can be respectively used simultaneously for sensitivity determination.

A diagnostic device for the above-described assays can be fashioned which can contain separate compartments of dry lyophilized spores of any of the *A. niger* mutants and/or its parent. The device can also contain an agar nutrient medium, e.g., YME, in a specially constructed or standard agar assay plate which can be packaged. Disc diffusion plates can also be included to allow the technician to saturate the disc with the medium to be tested and apply it to the agar medium after a specific *A. niger* microorganism spore suspension has been prepared and applied uniformly to the surface of the agar.

The disc results can be observed visually, or read with a spectrophotometer to measure intensity and compared to a known standard of FK-506, rapamycin or CsA to determine the $MIC_{50}$, the relative concentration of the known or unknown drug needed to inhibit 50% of the growth of the microorganism.

Following are examples of the invention which should not be considered as being limits on the scope or spirit of the invention.

EXAMPLE 1

Mutation Experiments—How To Make

The starting parent strain is Aspergillus *niger*, ATCC 6275 (NRRL 334) in the Merck culture collection as MF 442 and used in the antifungal screening panel. Growth and development of this parent organism is sensitive to low concentrations of FK-506 class of compounds, to rapamycin, and to cyclosporin A. Formation of black conidia indicating growth, is greatly retarded on solid media by all three classes of drugs, and a visually very striking yellow-colored zone, easily measurable by eye or image-analyzer, is formed around a disc to which each drug has been applied.

FK-506/Rapamycin Resistant Mutants

Spontaneous mutants resistant to FK-506/Rapamycin were obtained by spreading $10^5$/mL conidia of the parent Aspergillus niger ATCC No. 6275 on agar containing 4 g/1 yeast extract (Difco), 10 g/1 malt extract (Difco) and 4 g/1 dextrose (YME) and FK-506 at 20 µg/ml. From a number of dark, conidiated colonies growing within the profoundly inhibited black "lawn", several isolates were chosen. They were confirmed as being stably resistant to FK-506 at 20 µg/ml and tested at levels up to 100 µg/ml, to which they were also resistant. This strain was labelled (FK-506--R) (MF 5661) ATCC No. 74087.

A similar experiment using rapamycin at 1 µg/ml afforded colonies substantially identical to those obtained above, and resistant to levels of rapamycin up to 100 µg/ml. These were also cross-resistant to FK-506, and indistinguishable in morphology in the presence of FK-506 or rapamycin from the FK-506-R isolate described above. Likewise, the FK-506-R isolate was resistant to rapamycin up to 100 µg/ml.

Strains isolated on either FK-506 or rapamycin were grown in liquid medium (as above minus agar), and cell-free extracts prepared. They were examined for the presence of the major FK-506 binding protein, FKBP12, by assay using $^3$H-dihydro-FK560 (tritiated) and LIt20 resin (See Handschumacher, R. E. Science, supra). The method did not detect any active FKBP12. Thus, the FK-506R isolate lacks the binding protein FKBP12.

Cyclosporin A Resistant Mutants

The CsA-R mutant strain was isolated from *A niger* ATCC No. 6275 in a similar fashion as above using 1 µg/ml CsA in YME agar. The absence of active cyclophilin binding protein was demonstrated by an assay using tritiated cyclosporin A and LH20 resin (see the Science article above). The strain was labelled ATCC No. 74085 (MF 5659).

FK-D06/CsA/Rapamycin Resistant Mutant

The FK-506R,CsA-R strain ATCC No. 74086 (MF 5660) was isolated by plating the FK-506-R strain on 1 µg/ml CsA. A low frequency of conidiated colonies, now resistant to high levels of both drugs was found. The FK-506-R CsA-R strain lacked detectable binding activity with either 3H-FK-506 or 3H-CsA by the LIt20 method (see the Science article, supra).

EXAMPLE 2

How To Use

General disk assay for *Aspergillus niger* sensitivity to natural products of the FK506/rapamycin or *cyclosporin classes*.

The entire following assay is conducted under aseptic conditions.

*A. niger* Conidia are harvested after 5-8 days of growth at 30° C. on YME agar containing 4 g/1 yeast extract (Difco), 10 g/1 malt extract (Difco) and 4 g/1 dextrose which has been inoculated with either conidia or vegetative mycelium. They are harvested by lightly scraping the surface with a sterile cotton swab dampened in sterile water. The black conidia are rinsed off the swab in a vessel of sterile water to achieve a titer of $10^7$ to $10^8$ per ml., assessed by counting in a Petroll-Hauser counting chamber at appropriate dilution. This suspension may be kept at 4° C. for 1-14 days without appreciable loss of viability. $10^5$/mL conidia of each strain are uniformly spread on YME agar.

25 µL to 0.1 mL of broth, natural product extract, or unknown composition is pipetted onto sterile 6mm diameter paper disks and air-dried. Disks are placed on agar and the plates incubated at 25°-30° C. Observation of zone size and black or yellow pigmentation are made at 1-3 days. Where a zone of inhibition is present, a yellow color appears. Where no inhibition of growth is present, the coloration of the conidia present is black.

Utility of the Disc Diffusion Assay

Utilizing the above procedure, the FK-506/Rapamycin Resistant isolate, ATCC No. 74087 in conjunction with the sensitive parent, *A. niger* ATCC No. 6275, or with the CsA-Resistant strain, ATCC No. 74085, or both is used to detect and validate the presence in broths or any other medium of the FK-506 or rapamycin class of compounds.

Further, utilizing, the above procedure, the CsA-Resistant strain, in conjunction with the *A. niger* No. 6275, or with the FK-506-R ATCC No. 74087 strain, or both, is used to detect and validate the presence of the cyclosporin class of compounds.

Additionally, the doubly resistant strain ATCC No. 74086, is used as a counterscreen of a new immunosuppressant active found against *A. niger* No. 6275 to eliminate compounds of both the structural classes of FK-506/-rapamycin and cyclosporin classes simultaneously, indicating a new chemical class of immunosuppressants.

Further, the combination of ATCC No. 74087/6275 is used to distinguish between low and high FK-506 producing microorganisms by comparing their product outputs from equivalent amounts of microorganism and then determining that both exhibit no ZOI with the FK-506 resistant microorganism.

Combinations of the above assays can be used to test for the presence of both FK-506/Rapamycin and CsA types of activity concurrently. Other assays and combinations of the above will be obvious to one skilled-in-the-art from this disclosure and are deemed to be covered by this application.

What is claimed is:

1. A biologically pure form of an Aspergillus niger mutant identified as ATCC No. 74085.

2. A biologically pure form of an *Aspergillus niger* mutant identified as ATCC No. 74086.

3. A biologically pure form of an Aspergillus niger mutant identified as ATCC No. 74087.

4. A process for testing a compound or fermentation broth for cyclosporin immunosuppressant-type activity comprising the steps of: (1) contacting said compound or broth with: (a) *Aspergillus niger* ATCC No. 74085 mutant, and (b) *AspergillUS niger* ATCC No. 6275; (2) observing the conidiation characteristics of said ATCC No. 74085 mutant, which are positive in the presence of cyclosporin immunosuppressive-type activity, and (3) observing the conidiation characteristics of said ATCC No. 6275 which are negative in the presence of cyclosporin.

5. A process for testing a compound or fermentation broth for FK-506/rapamycin immunosuppressant-type activity comprising the steps of: (1) contacting said compound or broth with (a) *Aspergillus niger* ATCC No. 74087 mutant and (b) *Aspergillus niger* ATCC No. 6275, and (2) observing the conidiation characteristics of said ATCC No. 74087 mutant, which are positive in the presence of FK-506/ rapamycin immunosuppressive-type activity, and (3) observing the conidiation characteristics of said ATCC No. 6275 which are negative in the presence of FK-506/rapamycin type immunosuppressant activity.

6. A process for testing a compound or fermentation broth for FK-506/rapamycin type or cyclosporin A type immunosuppressant activity comprising the steps of: (1) contacting said compound or broth with (a) *Aspergillus niger* ATCC No. 74085 mutant (b) *Aspergillus niger* ATCC No. 74086 mutant; (c) *Aspergillus niger* ATCC No. 74087 mutant; (d) *Aspergillus niger* ATCC No. 6275; and (2) observing the conidiation characteristics of said mutants, which is: positive for ATCC No. 74086 and ATCC No. 74087, but negative for ATCC No. 74085 and ATCC No. 6275 in the presence of FK-506/rapamycin immunosuppressant-type activity; and positive for ATCC No. 74085 and ATCC No. 74086, but negative in the presence of ATCC No. 74087 and ATCC No. 6275 in the presence of cyclosporin A immunosuppressant-type activity.

* * * * *